United States Patent
Nishikawa et al.

(10) Patent No.: US 10,842,760 B2
(45) Date of Patent: Nov. 24, 2020

(54) SUSTAINED-RELEASE PREPARATION CONTAINING PSEUDOEPHEDRINE OR A PHARMACEUTICALLY ACCEPTABLE SALT THEREOF

(71) Applicant: SAWAI PHARMACEUTICAL CO., LTD., Osaka, Osaka (JP)

(72) Inventors: Yuki Nishikawa, Osaka (JP); Hiroaki Kikuoka, Osaka (JP); Michinori Oikawa, Osaka (JP); Hiroyuki Yamamoto, Osaka (JP); Tomoya Nakagawa, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/447,240

(22) Filed: Jun. 20, 2019

(65) Prior Publication Data
US 2019/0388363 A1    Dec. 26, 2019

(30) Foreign Application Priority Data
Jun. 21, 2018    (JP) .................................. 2018-117890

(51) Int. Cl.
| | |
|---|---|
| *A61K 31/137* | (2006.01) |
| *A61K 9/16* | (2006.01) |
| *A61K 31/445* | (2006.01) |
| *A61K 45/06* | (2006.01) |

(52) U.S. Cl.
CPC .......... *A61K 31/137* (2013.01); *A61K 9/1617* (2013.01); *A61K 9/1664* (2013.01); *A61K 9/1682* (2013.01); *A61K 31/445* (2013.01); *A61K 45/06* (2013.01)

(58) Field of Classification Search
CPC .. A61K 31/137; A61K 9/1617; A61K 9/1682; A61K 9/1664; A61K 31/445; A61K 45/06
See application file for complete search history.

(56) References Cited

U.S. PATENT DOCUMENTS

| | | | |
|---|---|---|---|
| 6,039,974 A | | 3/2000 | MacLaren et al. |
| 9,408,806 B2 * | | 8/2016 | Jain ........................ A61K 31/55 |
| 2008/0095843 A1 * | | 4/2008 | Nutalapati ............. A61K 9/209 |
| | | | 424/465 |
| 2017/0035656 A1 * | | 2/2017 | Luber .................. A61K 9/0056 |

FOREIGN PATENT DOCUMENTS

| | | |
|---|---|---|
| JP | 2002-511102 A | 4/2002 |
| JP | 2004-134160 A | 4/2004 |
| JP | 4344405 B2 | 10/2009 |
| JP | 2009-543780 A | 12/2009 |
| WO | 99/09957 A1 | 3/1999 |
| WO | WO 2016/130094  * | 8/2016 |

OTHER PUBLICATIONS

Hiroaki Okada et al. "Formulation design and manufacturing method for oral administration preparations, first volume", May 20, 2012, p. 303-306, cited in the present application, with partial English machine Translation.

Office Action issued for corresponding Japanese Patent Application No. 2018-117890 dated Jul. 7, 2020, along with a partial English machine translation, citing above references.

Maki et al., "Controlled Release from Wax Coated Granules by Tumbling Agglomeration Method", Journal of Powder Engineering, 1988, vol. 25, No. 6, pp. 338-343, along with an English Abstract and a partial English machine translation, cited in NPL No. 4.

* cited by examiner

*Primary Examiner* — Shirley V Gembeh
(74) *Attorney, Agent, or Firm* — Hauptman Ham, LLP

(57) ABSTRACT

A sustained-release preparation containing pseudoephedrine is provided comprising pseudoephedrine or a pharmaceutically acceptable salt thereof, and a hardened oil or stearic acid. The sustained-release preparation containing pseudoephedrine may contain a hardened oil or stearic acid in an amount of 100% by mass to 500% by mass with respect to the content of the pseudoephedrine or a pharmaceutically acceptable salt thereof. In addition, the sustained-release preparation containing pseudoephedrine may have a first part and a second part, the first part may contain the pseudoephedrine or a pharmaceutically acceptable salt thereof, and the first part or the second part may contain an optional active ingredient.

5 Claims, No Drawings

SUSTAINED-RELEASE PREPARATION CONTAINING PSEUDOEPHEDRINE OR A PHARMACEUTICALLY ACCEPTABLE SALT THEREOF

CROSS REFERENCE TO RELATED APPLICATIONS

This application is based upon and claims the benefit of priority from the prior Japanese Patent Application No. 2018-117890, filed on Jun. 21, 2018 the entire contents of which are incorporated herein by reference.

FIELD

The present invention relates to a sustained-release preparation containing pseudoephedrine or a pharmaceutically acceptable salt thereof.

BACKGROUND

Pseudoephedrine hydrochloride ((1S,2S)-2-methylamino-1-phenylpropan-1-ol monohydrochloride) is an a sympathomimetic drug and is widely used for the amelioration of nasal congestion caused by allergic rhinitis. For example, dellegra (registered trademark) combination tablet (Sanofi Corporation) is a sustained-release preparation having a sustained-release layer with controlled release of pseudoephedrine hydrochloride. Since the blood concentration of pseudoephedrine hydrochloride is maintained at an effective level for a long period of time, dellegra combination tablet keeps the effect of improving nasal congestion symptoms long.

A method of coating uncoated tablets or granules containing active ingredients with a polymer film, a method of uniformly dispersing a drug in a hydrophilic polymer, a method of uniformly dissolving or dispersing a drug in an oily release sustaining base such as wax and the like, a method of coating a core containing an osmotic pressure inducing agent and a drug with a semipermeable membrane such as cellulose acetate, and providing pores on the surface, and other methods are known as a technique for sustained release of solid preparations. Among them, the method of uniformly dissolving or dispersing a drug in an oil base is known as a method which is easy to design formulation as compared with other sustained release technologies because the structure is relatively simple ("Formulation design and manufacturing method for oral administration preparations, first volume" supervised by Hiroaki Okada, Yasuhiko Nakamura, published on May 20, 2012, p. 303-306).

For example, Japanese Patent No. 4344405 discloses a sustained-release pharmaceutical composition in which pseudoephedrine or a pharmaceutically acceptable salt thereof is dispersed in carnauba wax as a release sustaining base, and a melt granulation method is described as granulation method thereof. However, the melt granulation method includes the steps of melting and cooling carnauba wax, and the granulation takes longer time than other granulation methods. In addition, high temperature granulation may impair the stability of the drug substance. Furthermore, since melt granulation cannot be performed by a general granulator, the cost for introducing the granulator may be high. Hence, there is a need for a sustained-release preparation which can be prepared more easily and in which pseudoephedrine or pharmaceutically acceptable salt thereof is stably maintained.

SUMMARY

An object of the present invention is to provide a sustained-release preparation which can be prepared easily and in which pseudoephedrine or a pharmaceutically acceptable salt thereof is stably maintained.

According to one embodiment of the present invention, a sustained-release preparation containing pseudoephedrine which comprises pseudoephedrine or a pharmaceutically acceptable salt thereof, and a hardened oil or stearic acid is provided.

The sustained-release preparation containing pseudoephedrine may contain a hardened oil or stearic acid in an amount of 100% by mass to 500% by mass with respect to the content of pseudoephedrine or a pharmaceutically acceptable salt thereof.

The sustained-release preparation containing pseudoephedrine may have a first part and a second part, the first part may contain pseudoephedrine or a pharmaceutically acceptable salt thereof, and the first part or the second part may contain an optional active ingredient.

The second part may contain an optional active ingredient, and the optional active ingredient may be fexofenadine or a pharmaceutically acceptable salt thereof.

According to one embodiment of the present invention, a method for producing a sustained-release preparation containing pseudoephedrine, comprising mixing pseudoephedrine or a pharmaceutically acceptable salt thereof with a hardened oil or stearic acid, and granulating an obtained mixture by a wet granulation method is provided.

The wet granulation method may be a fluidized bed granulation method.

DESCRIPTION OF EMBODIMENTS

Hereinafter, the sustained-release preparation comprising pseudoephedrine or a pharmaceutically acceptable salt thereof and the method for producing the same according to the present invention will be described in detail. However, the sustained-release preparation comprising pseudoephedrine or a pharmaceutically acceptable salt thereof and the method for producing the same of the present invention is not construed as being limited to the description of the embodiments and examples given below.

As a result of investigations by the present inventors, it has been found that carnauba wax affects the stability of pseudoephedrine, and related substances increase during storage in a sustained-release preparation containing pseudoephedrine hydrochloride using carnauba wax as a release sustaining base described in Japanese Patent No. 4344405.

Further, as a result of investigations, the present inventors have newly found that a sustained-release preparation containing pseudoephedrine which contains pseudoephedrine or a pharmaceutically acceptable salt thereof and a hardened oil and a sustained-release preparation containing pseudoephedrine which contains pseudoephedrine or a pharmaceutically acceptable salt thereof and stearic acid can suppress generation of related substances during storage and can maintain the purity of pseudoephedrine, as compared with a sustained-release preparation containing pseudoephedrine which contains pseudoephedrine or a pharmaceutically acceptable salt thereof and carnauba wax.

Further, a sustained-release preparation containing pseudoephedrine described in Japanese Patent No. 4344405 has problems that the number of manufacturing steps is large, it is necessary to use a special granulator and the manufacturing takes a long time since it is produced by a melt granulation method. The present inventors have found that when a hardened oil or stearic acid is used as a release sustaining base, it can be manufactured by a wet granulation method with which manufacturing by a general granulator is possible. This makes it possible to reduce the number of manufacturing steps as well as the manufacturing time.

Furthermore, the present inventors have found that in granulating controlled-release particles containing pseudoephedrine or a pharmaceutically acceptable salt thereof by a wet granulation method, the granulation property is poor when carnauba wax is used as a release sustaining base, while the granulation property is good when a hardened oil or stearic acid is used as a release sustaining base.

The sustained-release preparation containing pseudoephedrine or a pharmaceutically acceptable salt thereof according to one embodiment of the present invention contains pseudoephedrine hydrochloride, and a hardened oil in an amount of 100% by mass to 500% by mass with respect to the content of pseudoephedrine hydrochloride. In addition, the sustained-release preparation containing pseudoephedrine or a pharmaceutically acceptable salt thereof according to one embodiment of the present invention more preferably contains a hardened oil in an amount of 350% by mass to 400% by mass with respect to the content of pseudoephedrine hydrochloride. In one embodiment of the present invention, Lubriwax (registered trademark)-101 of Freund Corporation is preferred as the hardened oil.

The sustained-release preparation containing pseudoephedrine or a pharmaceutically acceptable salt thereof according to one embodiment of the present invention contains pseudoephedrine hydrochloride, and stearic acid in an amount of 100% by mass to 500% by mass with respect to the content of pseudoephedrine hydrochloride. In addition, the sustained-release preparation containing pseudoephedrine or a pharmaceutically acceptable salt thereof according to one embodiment of the present invention more preferably contains stearic acid in an amount of 350% by mass to 400% by mass with respect to the content of pseudoephedrine hydrochloride.

In addition, although the carnauba wax is used as a release sustaining base in Japanese Patent No. 4344405, a hardened oil or stearic acid is used as a release sustaining base in the sustained-release preparation containing pseudoephedrine or a pharmaceutically acceptable salt thereof according to the present invention. Further, in Japanese Patent No. 4344405, although stearic acid is contained in a sustained-release layer, stearic acid is contained only as an anti-adhesive agent. Thus, the content of stearic acid in Japanese Patent No. 4344405 is different from the sustained-release preparation containing pseudoephedrine or a pharmaceutically acceptable salt thereof containing stearic acid in an amount of 100% by mass to 500% by mass with respect to the content of pseudoephedrine hydrochloride according to the present invention. Furthermore, the melt granulation method which is a type of a dry granulation method is used for manufacture of a sustained-release preparation containing pseudoephedrine in Japanese Patent No. 4344405, while a sustained-release preparation containing pseudoephedrine is manufactured using a simpler wet granulation method, especially a fluidized bed granulation method in the present invention.

The sustained-release preparation containing pseudoephedrine according to one embodiment of the present invention contains pseudoephedrine or a pharmaceutically acceptable salt thereof. As the pharmaceutically acceptable salt of pseudoephedrine, pseudoephedrine hydrochloride or pseudoephedrine sulfate can be used. In one embodiment, pseudoephedrine hydrochloride is preferred.

The sustained-release preparation containing pseudoephedrine or a pharmaceutically acceptable salt thereof of the present invention can be used as a single agent, but may be used as a combination agent combined with other active ingredients. That is, the sustained-release preparation containing pseudoephedrine of the present invention may have a first part and a second part, the first part may contain pseudoephedrine or a pharmaceutically acceptable salt thereof, and the first part or the second part may contain an optional active ingredient. The optional active ingredient includes, for example, but not limited to, fexofenadine hydrochloride.

Examples of the sustained-release preparation containing pseudoephedrine having a first part and a second part described above include, but not limited to, two or more multi-layered tablets containing a first sustained-release layer, a second sustained-release layer or an immediate-release layer, tablets obtained by tableting a mixture of first sustained-release granules, second sustained-release granules or immediate-release granules, and nucleated tablets having a sustained-release inner core, and a different sustained-release outer layer or an immediate-release outer layer. When the sustained-release preparation containing pseudoephedrine has a first part and a second part, the first part may contain pseudoephedrine or a pharmaceutically acceptable salt thereof, and the second part may contain fexofenadine or a pharmaceutically acceptable salt thereof.

The sustained-release preparation containing pseudoephedrine or a pharmaceutically acceptable salt thereof of the present embodiment may further contain one or more additives selected from an excipient, a binder, a disintegrant, a flavoring agent, a lubricant, a fluidizer and the like.

The excipient can be selected, for example, from sugar derivatives, starch derivatives, cellulose derivatives, gum arabic, dextran, pullulan, silicate derivatives, phosphate salts, carbonate salts, sulfate salts and the like. Examples of the sugar derivatives include lactose, sucrose, glucose, mannitol, erythritol, trehalose, maltose, xylitol, sorbitol and the like. Examples of the starch derivatives include corn starch, potato starch, α-starch, dextrin and the like. Examples of the cellulose derivatives include crystalline cellulose and the like. Examples of the silicate derivatives include light anhydrous silicic acid, synthetic aluminum silicate, calcium silicate, magnesium alum inometasilicate and the like. Examples of the phosphate salts include calcium hydrogen phosphate and the like. Examples of the carbonate salts include calcium carbonate, magnesium carbonate, sodium hydrogen carbonate and the like. Examples of the sulfate salts include calcium sulfate and the like. These excipients can be used alone or in combination of two or more.

The disintegrant can be selected, for example, from crospovidone, carmellose calcium, carmellose sodium, croscarmellose sodium, carmellose, cross-linked polyvinyl pyrrolidone, low substituted hydroxypropyl cellulose, various starches and the like. These disintegrants can be used alone or in combination of two or more.

The binder can be selected, for example, from hydroxypropyl cellulose, hydroxypropyl methylcellulose, polyvinyl pyrrolidone, polyvinyl alcohol, macrogol, compounds exemplified as the excipient above, and the like. These binders can be used alone or in combination of two or more.

The flavoring agent can be selected, for example, from sweeteners, acidulants, flavors and the like. As the sweetener, saccharin sodium, sucralose, thaumatin, acesulfame potassium, stevia extract, sucrose, aspartame and the like can be exemplified. Examples of the acidulant include citric acid, malic acid, tartaric acid and the like. As the flavor, menthol, lemon extract, orange extract and the like can be exemplified. These flavoring agents can be used alone or in combination of two or more.

The lubricant can be selected, for example, from stearic acid, stearic acid metal salts (calcium stearate, magnesium stearate, etc.), talc, colloidal silica, waxes (beeswax, spermaceti, etc.), boric acid, adipic acid, sulfates (sodium sulfate, etc.), glycol, fumaric acid, sodium stearyl fumarate, sodium benzoate, D,L-leucine, lauryl sulfates (sodium lauryl sulfate, magnesium lauryl sulfate, etc.), silicic acids (silicic acid anhydride, silicic acid hydrate, etc.), compounds exemplified as the excipient above, and the like. These lubricants can be used alone or in combination of two or more.

As the fluidizer, for example, light anhydrous silicic acid, colloidal silica, talc and the like can be exemplified.

The sustained-release preparation containing pseudoephedrine or a pharmaceutically acceptable salt thereof according to the present invention can suppress generation of related substances during storage and can maintain the purity of pseudoephedrine, by containing a hardened oil or stearic acid in an amount of 100% by mass to 500% by mass, more preferably 350% by mass to 400% by mass with respect to the content of pseudoephedrine or a pharmaceutically acceptable salt thereof, as explained above.

(Production Method)

The sustained-release preparation containing pseudoephedrine according to the present invention is characterized in that pseudoephedrine or a pharmaceutically acceptable salt thereof is blended with a hardened oil or stearic acid. A tablet containing pseudoephedrine or a pharmaceutically acceptable salt thereof and a hardened oil or stearic acid can be manufactured according to a production method known in the pharmaceutical field.

For example, a predetermined amount of pseudoephedrine hydrochloride (for example, 60 mg) is mixed with a hardened oil or stearic acid and light anhydrous silicic acid, and an aqueous solution containing a predetermined amount of hydroxypropyl cellulose is added, granulated and dried, to obtain granules. The obtained granules are sieved and mixed to obtain a powder before tableting. By tableting the obtained powder, it is possible to produce a tablet containing pseudoephedrine or a pharmaceutically acceptable salt thereof according to the present invention. Among these operations, wet granulation methods such as fluidized bed granulation, agitation granulation and tumbling granulation are preferable as the granulation method, and among these, fluidized bed granulation is preferable. In addition, tableting can be performed by a conventional method using a commercially available tableting machine.

Furthermore, in the case of production of a two-layered tablet combining a layer containing pseudoephedrine or a pharmaceutically acceptable salt thereof with a layer containing other active ingredients as the sustained-release preparation containing pseudoephedrine or a pharmaceutically acceptable salt thereof, it may be permissible that a powder before tableting containing pseudoephedrine or a pharmaceutically acceptable salt thereof is compressed to form a first layer, and further, a powder before tableting containing other active ingredients is compressed on the first layer to form a second layer.

(All Related Substance)

In the present specification, as stability evaluation, liquid chromatography is used to evaluate the purity of pseudoephedrine. The total area of the detected peaks is taken as 100%, and the ratio of the peak area of related substances derived from pseudoephedrine to the total area is calculated, to determine the amount of all related substances (%).

EXAMPLES

The sustained-release preparation containing pseudoephedrine or a pharmaceutically acceptable salt thereof according to the present invention described above will be illustrated in more detail referring to specific examples and test results.

Example 1

In a tumbling fluidized coating machine (Powrex Corporation, MP-01), 72.0 g of pseudoephedrine hydrochloride, 272.4 g of a hardened oil (Freund Corporation, Lubriwax-101) and 1.2 g of light anhydrous silicic acid (Fuji Silysia Chemical Ltd., Adsolider 101) were mixed, and a 8% aqueous solution containing 12.6 g of hydroxypropyl cellulose (Nippon Soda Co., Ltd., HPCL) was sprayed onto this, and these were granulated and dried. The resulting granules were sieved with No. 22 sieve, and 1.50 mg of magnesium stearate (Taihei Chemical Industrial Co., Ltd.) was added as an external lubricant to 298.5 mg of the sieved material, these were finally mixed, to obtain a powder before tableting. This powder was tableted by a tableting machine to obtain tablets which was 300.0 mg per tablet.

Example 2

As Example 2, 272.4 g of stearic acid (NOF Corporation) was used in place of 272.4 g of a hardened oil. Other production steps are as in Example 1.

Comparative Example 1

As Comparative Example 1, 272.4 g of carnauba wax (Nippon Wax Co., Ltd., Polishing Wax-105) was used in place of 272.4 g of a hardened oil. Other production steps are as in Example 1.

In the preparation of Comparative Example 1 using carnauba wax as a base, the powder coagulated and did not flow, and the granulation was poor, at the time of granulation.

The sustained-release preparations containing pseudoephedrine or a pharmaceutically acceptable salt thereof of Example 1, Example 2 and Comparative Example 1 were stored for 2 weeks under conditions of 60° C. and 60% humidity. The amount (%) of all related substances was measured for each sustained-release preparation containing pseudoephedrine or a pharmaceutically acceptable salt thereof after storage.

(All Related Substance)

The amount of all related substances was calculated using the liquid chromatography shown below to evaluate the purity of pseudoephedrine. Assuming that the total area of the detected peaks was 100%, the ratio of the peak area of related substances derived from pseudoephedrine to the total area was calculated, to obtain the amount (%) of all related substances.

(HPLC Measurement Condition)

Using a column with octadecylsilylated silica gel as a carrier, a mixture of pH 2.5 phosphate buffer and methanol was used as a mobile phase. The peak was detected using an ultraviolet absorptiometer with a wavelength of 215 nm.

Table 1 shows the measurement results of all related substances.

TABLE 1

| | All related substances (%) |
|---|---|
| Example 1 | 0.02 |
| Example 2 | 0.09 |
| Comparative Example 1 | 0.44 |

In the sustained-release preparation containing pseudoephedrine hydrochloride of Comparative Example 1 containing carnauba wax, 0.44% of all related substances were detected. On the other hand, in the sustained-release preparation containing pseudoephedrine hydrochloride of Example 1 containing a hardened oil, 0.02% of all related substances were detected. In addition, in the sustained-release preparation containing pseudoephedrine hydrochloride of Example 2 containing stearic acid, 0.09% of all related substances were detected. That is, it became clear that in Example 1 and Example 2, generation of all related substances after storage is suppressed as compared with Comparative Example 1.

Thus, by containing a hardened oil or stearic acid in an amount of 100% by mass to 500% by mass, more preferably 350% by mass to 400% by mass with respect to the content of pseudoephedrine or a pharmaceutically acceptable salt thereof, it is possible to improve the stability during storage in a sustained-release preparation containing pseudoephedrine or a pharmaceutically acceptable salt thereof.

Next, a dissolution test was performed for the sustained-release preparations containing pseudoephedrine hydrochloride obtained in Example 1 and Example 2 and Comparative Example 1.

(Dissolution Test)

According to the second method (paddle method) of the dissolution test method of the Japanese Pharmacopoeia 17-th, the dissolution test first solution was used as a test solution, and the dissolution rate (%) of pseudoephedrine after 5 minutes, after 10 minutes, after 15 minutes, after 30 minutes, after 45 minutes, after 60 minutes, after 120 minutes, after 180 minutes, after 300 minutes, after 420 minutes, after 540 minutes and after 720 minutes was calculated by the following HPLC measurement method.

(HPLC Measurement Condition)

Using a column with octadecylsilylated silica gel as a carrier, a mixture of pH 2.5 phosphate buffer and acetonitrile was used as a mobile phase. The peak was detected using an ultraviolet absorptiometer with a wavelength of 210 nm.

Table 2 shows the results of the dissolution test.

TABLE 2

| | Dissolution rate (%) | | | | | | |
|---|---|---|---|---|---|---|---|
| | Time (min) | | | | | | |
| | 0 | 5 | 10 | 15 | 30 | 45 | 60 |
| Example 1 | 0 | 11.4 | 16.1 | 19.8 | 28.1 | 34.3 | 39.7 |
| Example 2 | 0 | 13.7 | 20.3 | 25.4 | 37.1 | 45.7 | 53 |
| Comparative Example 1 | 0 | 14.2 | 20 | 24.6 | 34.4 | 41.7 | 47.5 |

TABLE 2-continued

| | Dissolution rate (%) | | | | | |
|---|---|---|---|---|---|---|
| | Time (min) | | | | | |
| | 120 | 180 | 300 | 420 | 540 | 720 |
| Example 1 | 55.8 | 67.05 | 83.9 | 93.2 | 97.8 | 99.8 |
| Example 2 | 75.4 | 89.1 | 98.6 | 100.2 | 100.5 | 99.6 |
| Comparative Example 1 | 64.3 | 75.95 | 91.5 | 99.4 | 102.3 | 104.1 |

The results of the dissolution test demonstrated that the sustained-release preparations containing pseudoephedrine hydrochloride—of Example 1, Example 2 and Comparative Example 1 exhibited sustained-release.

It is understood that, of course, other functions and effects different from the functions and effects provided by the aspects of the embodiments described above are also provided by the present invention, as long as they are apparent from the description of the present specification or can be easily predicted by those skilled in the art.

According to the present invention, a sustained-release preparation which can be simply produced and in which pseudoephedrine or a pharmaceutically acceptable salt thereof is kept stably is provided.

What is claimed is:

1. A sustained-release preparation containing pseudoephedrine comprising:
    pseudoephedrine or a pharmaceutically acceptable salt thereof, and
    a hardened oil or stearic acid,
    wherein an amount of the hardened oil or the stearic acid ranges from 350% by mass to 500% by mass with respect to an amount of the pseudoephedrine or the pharmaceutically acceptable salt thereof.

2. The sustained-release preparation containing pseudoephedrine according to claim 1, having a first part and a second part, wherein
    the first part contains the pseudoephedrine or a pharmaceutically acceptable salt thereof, and
    the first part or the second part contains an optional active ingredient.

3. The sustained-release preparation containing pseudoephedrine according to claim 2, wherein
    the second part contains the optional active ingredient, and the optional active ingredient is fexofenadine or a pharmaceutically acceptable salt thereof.

4. A method for producing a sustained-release preparation containing pseudoephedrine, comprising
    mixing pseudoephedrine or a pharmaceutically acceptable salt thereof with a hardened oil or stearic acid, and
    granulating an obtained mixture by a wet granulation method,
    wherein an amount of the hardened oil or the stearic acid ranges from 350% by mass to 500% by mass with respect to an amount of the pseudoephedrine or the pharmaceutically acceptable salt thereof.

5. The method for producing a sustained-release preparation containing pseudoephedrine according to claim 4, wherein
    the wet granulation method is a fluidized bed granulation method.

* * * * *